United States Patent [19]

Olsen

[11] Patent Number: 4,508,827
[45] Date of Patent: * Apr. 2, 1985

[54] MOLECULAR CLONING VECTORS FOR USE IN GRAM-NEGATIVE BACTERIA

[75] Inventor: Ronald H. Olsen, Ann Arbor, Mich.

[73] Assignee: Microlife Technics, Inc., Sarasota, Fla.

[*] Notice: The portion of the term of this patent subsequent to Feb. 15, 2000 has been disclaimed.

[21] Appl. No.: 462,630

[22] Filed: Jan. 31, 1983

Related U.S. Application Data

[63] Continuation-in-part of Ser. No. 147,563, May 8, 1980, Pat. No. 4,374,200.

[51] Int. Cl.³ .................... C12N 1/20; C12N 1/00; C12N 15/00; C12P 21/00; C12P 19/34; C12P 21/02; C12R 1/385
[52] U.S. Cl. ................................. 435/253; 435/68; 435/91; 435/317; 435/172.3; 435/875; 435/70; 935/29; 935/56; 935/60; 935/72
[58] Field of Search ............... 435/68, 317, 875, 253, 435/91, 70, 172.3

[56] References Cited

U.S. PATENT DOCUMENTS 3,813,316  5/1974  Chakrabarty ............ 435/248
4,237,224 12/1980  Cohen et al. ............ 435/68
4,278,765  7/1981  Debabov et al. ......... 435/172.3
4,374,200  2/1983  Olsen .................... 435/91

OTHER PUBLICATIONS

Bolivar, R., Gene 4:121-136 (1978).
Royle, P. Matsumoto, and B. Holloway, J. Bacteriol. 145:145-155 (1981).
Bolivar, R. R. Rodriguez, P. Greene, M. Betlach, H. Heyneker, H. Boyer, J. Cross, and B. Falkow, Gene 2:95-113 (1977).
Olsen, R. and P. Shipley, J. Bacteriol. 113:772-780 (1972).
Stanier, R., N. Palleroni, and M. Doudoroff, J. Gen. Microbiol. 43:159-271 (1966).
Guerry, LeBlanc and Falkow, J. Bacteriol. 116:1064-116:1066 (1973).
Hansen and Olsen, J. Bacteriol. 135:227-238 (1978).
Mercer and Loutit, J. Bacteriol. 140:37-42 (1979).
Davis, Botstein and Roth, In Advanced Bacteriol Genetics: A Manual for Genetic Engineering, Cold Spring Harbor Lab., (1980 pp. 134-137).

Primary Examiner—Lionel M. Shapiro
Assistant Examiner—James Martinell
Attorney, Agent, or Firm—Ian C. McLeod

[57] ABSTRACT

Improved cloning vectors derived from pRO1614 are described. One of these vectors, pRO1727, is suitable for cloning using DNA cleaved with the restriction endonuclease, PstI, and allows selection for the recovery of recombinant plasmids using tetracycline resistance. The cloning efficiency observed for pRO1727 is higher than described previously for pRO1614 and the host range of this vector is now restricted to Pseudomonas bacteria. Another vector, designated pRO1729, is described and developed from pRO1727 by deletion of a portion of its DNA and incorporation of a segment of DNA which encodes for resistance to the antibiotic, chloramphenicol. The chloramphenicol resistance determinant has a cleavage site for restriction endonuclease EcoRI within its chloramphenicol resistance determinant. Thus, DNA cloned into this site results in the loss of chloramphenicol resistance which can be detected subsequent to a cloning experiment. Both pRO1727 and pRO1729 are more useful in Pseudomonas for cloning than pRO1614.

7 Claims, 3 Drawing Figures

MOLECULAR CLONING VECTORS FOR USE IN GRAM-NEGATIVE BACTERIA

CROSS REFERENCE TO RELATED APPLICATION

This application is a continuation-in-part of my pending application Ser. No. 147,563, filed May 8, 1980 now U.S. Pat. No. 4,374,200.

BACKGROUND OF THE INVENTION

1. Field of the Invention

The present invention relates to cloning vectors derived in part from the molecular cloning vector-plasmid, pRO1614 described in my application Ser. No. 147,563. In particular, the present invention has greater utility for cloning in Gram negative bacterial strains, especially the genus Pseudomonas.

2. Prior Art

The basic prior art is described in U.S. Pat. No. 4,237,224 to Cohen and Boyer. The pioneering effort described in this patent provided the starting point for the present invention and is familiar to all those skilled in the art. There is a large body of prior art which is directly related to this patent. The patent terminology is generally used herein. U.S. Pat. No. 4,278,765 to Debabov et al. describes other vectors and recombinant plasmids. U.S. Pat. No. 3,813,316 to Chakrabarty describes multiple plasmid containing Pseudomonas and the method for their preparation.

In the method of my application Ser. No. 147,563 as in the method of the Cohen and Boyer patent, indirect selection of recombinant plasmids which are transformed into a recipient host is described. This method involves the selection for a genetic marker in the transformed bacteria and the selection for the particular phenotypic trait. The selection method is laborius and time consuming in obtaining a particular phenotypic trait and provides one important reason why genetic research has been expensive. The reason for this result is that the transformation frequencies are low (or nonexistent) in relation to a particular gene in a recombinant plasmid.

OBJECTS

It is an object of the present invention to provide single cloning vectors for use in molecular cloning with a wide variety of restriction endonucleases, instead of several cloning vectors used singly. It is also an object of this invention to incorporate an additional antibiotic resistance gene into the vector with an endonuclease enzyme site within its structure so that the insertion of cloned DNA into this site results in the loss of expression for the antibiotic resistance determinant. Further still it is an object of the present invention to provide vectors useful for direct selection. These and other objects will become increasingly apparent by reference to the following description and the drawings.

IN THE DRAWINGS

SUMMARY OF THE INVENTION

Figure 1:
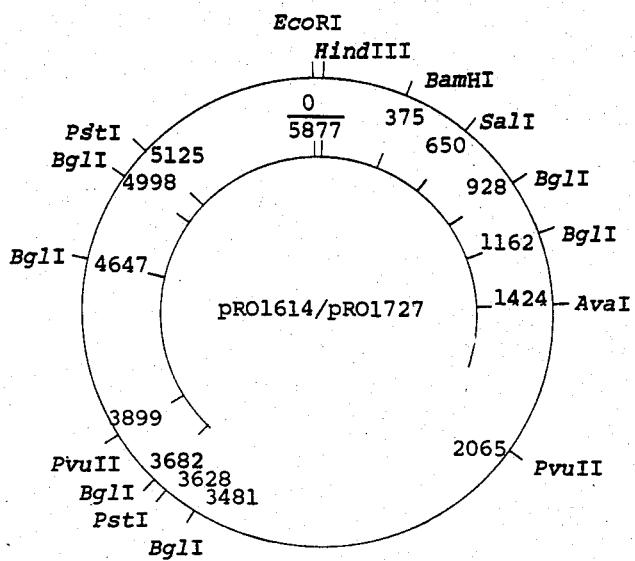
FIG. 1 is a physical map of plasmid pRO1727 showing its relationship to its progenitor, plasmid pRO1614.
Figure 2:
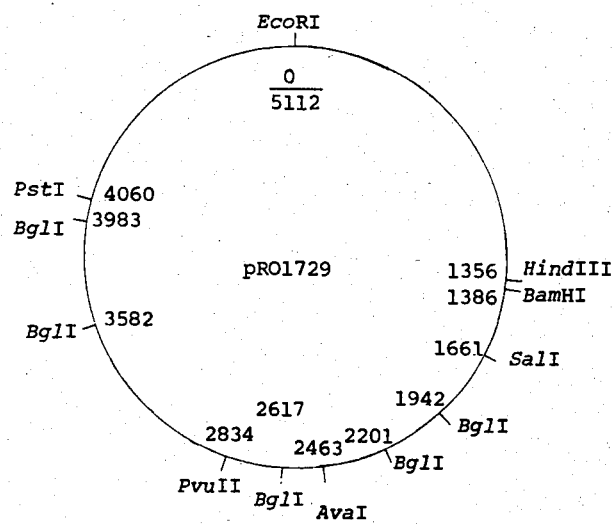
FIG. 2 shows the physical map of plasmid pRO1729 which was derived from in part from pRO1727 and in part from plasmid pBR325.

The present invention relates to a recombinant deoxyribonucleic acid plasmid pRO1727 as a cloning vector, having a molecular size of about 5.9 kilobase pairs and a restriction endonuclease cleavage map as shown in FIG. 1, either alone or ligated to other deoxyribonucleic acid segments. The present invention also relates to a recombinant deoxyribonucleic acid plasmid pRO1729 having a molecular size of about 2.9 kilobase pairs amd a restriction endonuclease cleavage map as shown in FIG. 2, alone alone or ligated to other deoxyribonucleic acid segments.

The present invention thus relates to improved vectors derived from the cloning vector pRO1614. A single vector, pRO1727 or pRO1729, may be utilized for the molecular cloning wherein the vector and hetero-DNA are cleaved with restriction endonuclease PstI and other cleavage enzymes corresponding to cleavage sites on the vectors. Therefore, with the new vectors, recombinant plasmids formed using PstI may be selected initially in transformed bacteria for antibiotic resistance (tetracycline for pRO1727, tetracycline or chloramphenicol for pRO1729). Accordingly, indirect selection may now be used for the recovery of recombinant plasmids formed with PstI-cleaved DNA. This procedure has been shown previously to optimize the isolation of recombinant plasmids.

The incorporation of an additional antibiotic resistance determinant specifying resistance to chloramphenicol into pRO1727 produces pRO1729. The resistance in pRO1729 is suppressed when DNA cleaved with restriction endonuclease, EcoRI is incorporated into the EcoRI site located within this antibiotic resistance determinant.

Finally, the present invention(s) relate to a change in the bacterial host range of the vectors, pRO1727 and pRO1729, in relation to their progenitor, pRO1614. The objects of the present invention, pRO1727 and pRO1729, cannot be maintained by the bacterium *Escherichia coli* because of the deletion of certain genes from pRO1614. Accordingly, these vectors have additional utility in such cases wherein it is desirable to restrict the dissemination of these vectors and their cloned hetero-DNA to some other bacterial species that are common inhabitants of the intestinal tract of higher life forms.

As described in Serial No. 147,563 the progenitor of the vectors pRO1727 and 1729 was a small, multi-copy plasmid, pRO1600 as carried in *Pseudomonas aeruginosa* NRRL-B-12124, found in the PAO strain which had acquired plasmid RP1 in a mating experiment. The plasmids pRO1613 and pRO1614 were developed from pRO1600 and are carried in *Pseudomonas aeruginosa* NRRL-B-12126 and 12127, respectively. They are freely available to the public upon request by strain and number designation.

The bacterial host range of vectors produced from pRO1600 resemble that for plasmid RP1. Derivative-plasmid pRO1613, for cloning DNA was cleaved with restriction endonuclease PstI. Plasmid, pRO1614, was formed by deleting part of pRO1613 and fusion with plasmid pBR322 from *Escherichia coli*. Plasmid pRO1614 utilizes cloning-sites within the tetracycline resistance region of pBR322.

A host-vector system for *Pseudomonas putida* and particularly for *Pseudomonas aeruginosa* PAO was used. Chromosomal DNA from strain PAO was cloned and a gene-bank formed which contained numerous independently isolated chromosome-vector recombinant plasmids using the method described in my application Serial No. 328,957, filed Dec. 9, 1981. This was done using restriction endonuclease, PstI, for cleavage of the vector, pRO1727, and the chromosomal DNA derived from strain PAO as described hereinafter.

DERIVATION OF CLONING VECTORS

Molecular cloning of chromosomal DNA using plasmids developed for that purpose has been reported for a variety of bacterial species. In most instances, the utility of the plasmid cloning vector derives from the inactivation of an antibiotic resistance determinant of the vector as a consequence of the insertion of a piece of hetero-DNA from the chromosome into a site on the vector cleaved by a restriction endonuclease. Thus, the continuity of the vector's gene and hence its expression is interrupted by insertion of foreign pieces of DNA. One of the widely used plasmid vectors of this kind is plasmid pBR325 which has the advantage of a unique restriction endonuclease site within its antibiotic resistance determinants for ampicillin resistance, tetracycline resistance and chloramphenicol resistance (Bolivar, R., Gene 4:121-136 (1978)). However, the host range of pBR325 is limited to *Escherichia coli* and related bacterial strains prohibiting its usefulness in bacteria with disparate properties.

The development of the cloning vectors is pRO1727 and 1729 described which function in the bacterial genus Pseudomonas in the manner of the vectors pBR322 and pBR325 used in *Escherichia coli*.

GENE BANK METHOD FOR DIRECT SELECTION

Application Ser. No. 328,957 relates to an improvement in the gene splicing method wherein chromosomal DNA is partially and randomly cleaved into fragments with a restriction enzyme and spliced into a cleaved vector thereby joining the chromosomal DNA fragments to the vector to form a recombinant plasmid which comprises mechanically fragmenting concentrated chromosomal DNA in the absence of bacterial cells into multiple fragments of randomly varying lengths; and partially cleaving with a restriction enzyme and joining the mechanically fragmented and cleaved chromosomal DNA with the cleaved vector to form a bank of recombinant plasmids of varying sizes.

Further Ser. No. 328,957 relates to a preserved recombinant plasmid bank adapted for transformation into a bacteria and then selection for particular recombinant plasmids, the bank containing multiple random length mechanically fragmented chromosomal DNA fragments having an average length between 0.1 and 20 daltons $\times 10^6$ recombined with a vector and the plasmids being adapted for transformation into a bacterium having a particular mutant gene trait allowing for selection.

Finally Ser. No. 328,957 relates to certain novel transformed hosts of the genus Pseudomonas into which the recombinant plasmids prepared by the method are transformed. The recombinant plasmids are in a gene bank formed as a result of the initial fragmenting of the chromosomal DNA and are highly transformable. Virtually any gene from the chromosomal DNA can be found in the collection of recombinant plasmids and can be selected using conventional selection techniques with plasmid free, auxotrophic bacteria for the transformation and defined media. The recombinant plasmids of the "closed" coiled or "super coiled" like a spring which promotes highly efficient transformation.

Because of the high transformation frequency, selection can be made directly for almost any particular phenotypic or gene trait from the pool of super coiled DNA recombinant plasmids. This contrasts with the prior art method wherein indirect selection is made based upon a particular phenotypic marker in the chromosomal DNA usually in antibiotic marker or directed selection of rare closed circular DNA plasmids. The transformants in the prior art method are then tested for acquisition of a particular associated marker within the transformants along with the antibiotic marker, such as the ability to produce an essential amino acid. Many times the desired marker is not formed. In the method of the present invention the probability is great that the particular marker can be selected directly. The result is a considerable savings of time and money in obtaining desirable transformants.

A vortex mixer (such as a Vortex Genie ® Fisher Scientific Company) is preferably used to fragment the chromosomal DNA. An eccentric cup oscillates, causing a vortex in a test tube shaped container. The chromosomal DNA because of its length and relatively greater inertia with respect to the moving liquid breaks into relatively small fragments which have an average length between about 10 and $20 \times 10^6$ daltons. The fragmenting is accomplished essentially by whipping the long strands of chromosomal DNA.

DESCRIPTION OF SPECIFIC EMBODIMENTS

Materials and Methods

Bacterial strains and plasmids. The relevant properties of the bacterial strains and plasmids used are listed in Table 1.

TABLE 1

Bacteria and Plasmids

| | Genotype | Reference or Source |
|---|---|---|
| Bacterial Strain | | |
| *Pseudomonas aeruginosa* strain PAO2 | ser-3 | (1) |
| *Pseudomonas putida* strain PPO131 | his-1 | (2) |
| *Escherichia coli* strain ED8654 | Met$^-$,k$_m^-$,k$_r^-$ | (3) |
| Plasmid | | |
| pBR322 | CbR, TcR | (4) |
| pBR325 | CbR, TcR, CmR | (5) |
| pRO1614 | CbR, TcR | parent application Serial No. 147,563 as carried in *Pseudomonas aeruginosa* |

TABLE 1-continued

Bacteria and Plasmids

| Genotype | Reference or Source |
|---|---|
| | NRRL-B-12127 |

Marker abbreviations: Bacterial Strains ser, serine; his, histidine. All of the strains and plasmids are available from the University of Michigan Medical School, Ann Arbor, Michigan, care of Ronald H. Olsen. The known strains and plasmids are readily available to those skilled in the art. Auxotrophs are obtained by selection.
(1) Royle, P. H, Matsumoto, and B. Holloway. J. Bacteriol. 145: 1145–155 (1981). Mutant of ATCC 15692 requiring serine.
(2) Mutant of ATCC 12633 selected for requiring the amino acid histidine.
(3) Culture collection of R. H. Olsen, University of Michigan Medical School.
(4) Bolivar, R., R. Rodriguez, P. Greene, M. Betlach, H. Heyneker, H. Boyer, J. Cross, and B. Falkow. Gene 2: 95–113 (1977).
(5) Bolivar, R. Gene, 4: 121–136 (1978).

$k_r^-$ is deficient in restriction of hetero DNA, $k_m^-$ is deficient in the modification of DNA, CbR is carbenicillin resistant, TcR is tetracycline resistant, CmR is chloramphenicol resistant.

Media. Minimal medium (VBG) and complex medium (TN) were prepared as described in Olsen, R., and P. Shipley, J. Bacteriol. 113:772–780 (1973). When nutritional selection for transformants was done, amino acid requirements were satisfied by the addition of these components to a final concentration of 5 mM. Antibiotic supplements were as described in the tables. Selection or indirect testing for the acquisition of catabolic markers was done using a minimal medium (MMO) described previously for this purpose (Stanier, R., N. Palleroni, and M. Doudoroff, J. Gen. Microbiol. 43:159–271 (1966). Carbon sources were incorporated into MMO at a final concentration of 0.2 percent.

Preparation of DNA. Plasmid DNA was prepared using a modification of the method of Guerry, LeBlanc and Falkow, J. Bacteriol. 116:1064–1066 (1973). Cells were grown overnight on the surface of TN-agar medium plates. In some cases, carbenicillin (Cb. 0.5 mg per ml) was included in the medium to maintain selection for plasmids. The cells were harvested from the surface of the plates by adding 5 ml sterile water to each plate and scraping with a glass rod. These suspensions were decanted and pooled into a bottle which was shaken vigorously to disperse clumps of cells. The cell suspension was then centrifuged at ambient temperature and the pellets suspended in TS buffer (9% sucrose—0.05 M Tris, pH8) (10 ml buffer for each centrifuge tube with about $1.5 \times 10^{10}$ cells). The following additions and manipulations were then done with each suspension. Na$_2$EDTA (0.5 M, pH8.0) which functions as a chelating agent for metal ions was added to a final concentration of 0.08 M. This was followed immediately by the addition of lysozyme (10 mg per ml in 0.25 M tris, pH8.0) to a final concentration of 0.77 mg per ml. The tubes were then briefly mixed on a vortex mixer (Vortex Genie ® Fisher Scientific Company) and incubated at 37° C. for 5 minutes. Following this, sodium dodecyl sulfate (SDS, 15 percent in distilled water) was added to a final concentration of 2 percent. The tubes were inverted slowly several times to mix and then incubated in a water bath for 5 minutes at 37° C. During this time they were removed several times and slowly inverted to promote lysis of the cells. Finally, 5M NaCl in distilled water was added to a final concentration of 0.95M and mixed into the suspension by several gentle inversions. The tubes were then placed into an ice-water bath for 10 minutes followed by storage overnight at 4° C. Precipitation of chromosome, harvest of plasmid DNA and CsCl-ethidium bromide centrifugation was then done as described previously by Hansen and Olsen, J. Bacteriol. 135:227–238 (1978). DNA was stored frozen in TO buffer (Tris 10 mM–1 mM Na$_2$EDTA, pH 8) and thawed slowly in ice water when used.

Recombinant plasmids were surveyed for their size using cells harvested from a path of growth on selective medium and lysis of cells by the procedure of Hansen and Olsen.

Chromosomal DNA was harvested from *Pseudomonas aeruginosa* strain PAO 1 which had been selected for resistance to rifampin (50 μg per ml) in the laboratory. The procedure described above (modification of Guerry et al.) was used for chromosomal DNA too except that the lysed cell suspensions were given two 30 sec pulses at full speed on a vortex mixer prior to the addition of 5M NaCl. This was done to fragment the chromosome in the manner of application Ser. No. 328,957. These lysed suspensions were then salt-precipitated followed by DNA precipitation and CsCl-ethidium bromide centrifugation as described previously for plasmid DNA. Transformation. Pseudomonands were transformed using a modification of the method of Mercer and Loutit, J. Bacteriol. 140:37–42(1979). Bacteria were grown overnight on TN agar and a portion then inoculated into TN broth with incubation for 2 to 3 hours reaching a cell density of $1 \times 10^8$ per ml. The cells were centrifuged at 4° C. and the pellet suspended in one-half volume cold sterile MgCl$_2$ (0.15M in distilled water). The pellet was dispersed and held in an ice-water bath for an additional 5 minutes. The cells were centrifuged and the pellet suspended as before but then held in the ice-water bath for 20 minutes. The cells were centrifuged again and the pellet suspended in one-tenth volume cold MgCl$_2$ (0.15M). Transforming-DNA (10 to 50 μl) was placed in a cold centrifuge tube and 0.2 ml of the above cells added with mixing. This mixture was incubated in an ice-water bath for 60 minutes followed by a heat-pulse in a water bath at 37° C. for 3 minutes while gently swirling the tube. The DNA-cell mixture was then placed immediately in an ice-water bath and incubated for 5 minutes. After this, 0.5 ml TN broth was added and the suspension incubated at 37° C. for 1 to 2.5 hours. The cells were then plated on selective medium and the plates were incubated at appropriate temperatures for 48 hours.

*Escherichia coli* was transformed using a modification of the method of Davis, Botstein and Roth, In Advanced Bacterial Genetics: a manual for genetic engineering. Cold Spring Harbor Laboratory, Cold Spring Harbor (1980 pp 134–137). For this, bacteria were grown as above and cultures chilled at the end of the growth period in an ice-water bath for 10 minutes. The cells were then centrifuged at 4° C. and pellets were suspended in one-half volume CTG buffer (CaCl$_2$, 50 mM; glycerol, 10 percent, thymidine, 50 μg per ml). The cells were dispersed and incubated 5 minutes in a bath at 0° C. They were then centrifuged and pellets were suspended at one-twentieth volume of the original culture. 0.2 ml cells were added to tubes which contained 20 to 100 μl DNA and mixed; these were held 3 minutes in an ice-water bath. The tubes were then transferred to a 45° C. water bath and slowly swirled for 2 minutes; they were then placed in an ice-water bath for 5 minutes. Following this, 0.5 ml of TN broth was added and the mixture was incubated at 27° C. for 0.5–2.5 hours. Samples of these transformation mixtures were then plated at 37° C. on selective medium. For both transformation procedures, all materials, including pipettes were at 4° C. unless otherwise noted.

Enzymes. Restriction endonuclease (Bethesda Research Laboratories, Rockville, MD) digestion and ligation were done as is shown in the prior art Digested DNA to be ligated was incubated for 20 hours at 17° C. Ligations were done in a volume of 20 μl or less. In some experiments, this required concentration of cleaved DNA by ethanol precipitation prior to the addition of ligase and buffer. These ligation mixture were used for transformation as described above and in the Tables.

Development of cloning-vector pRO1727. The starting material for this development was vector, pRO1614. The objective here was to obtain a derivative of pRO1614 which would have a region of its DNA deleted within which was located a cleavage site for restriction endonuclease PstI not known previously to be associated with any important phenotypic trait of the vector. A physical map for plasmid pRO1614 is shown in FIG. 1 in closed form outside pRO1727 in unclosed form. The PstI cleavage site in question here is shown at base pair coordinate 3628. The initial approach was to cleave plasmid pRO1614 with restriction endonuclease PvuII and re-form a plasmid after deletion of the piece traversing the distance between coordinates 2065 to 3899. When this was done and cleaved DNA was ligated, transformed into PAO2, plasmid DNA harvested and analyzed, an unexpected result obtained. One such plasmid, designated pRO1727, showed a deletion in the region of the PstI site at coordinate 3628 through the PvuII site at coordinate 2065. Thus, although a deletion occurred, it was not precisely at the location anticipated. However, it did accomplish the desired objective. A physical map of this resultant plasmid, pRO1727, is shown in FIG. 1 as the innermost ring in comparison to pRO1614 (outer ring). The plasmid has a size of about 4.0 kilobase pairs. The region of DNA from pRO1614 which has been deleted in pRO1727 includes genes for replication functions of plasmid pBR322 as described in application Serial No. 147,563. Thus, the replication activities of plasmid pBR322 required for maintenance of pBR322 in *Escherichia coli* have been deleted. The ability of pRO1727 to be maintained in *Escherichia coli* was tested. For this procedure, pRO1727 DNA was prepared from PAO2(pRO1727) and transformed into *Escherichia coli* EP 8654. When this was done several times, no transformants were obtained. Accordingly, a substantial alteration of the plasmid has occurred which now limits its host range to Pseudomonas. This changed property of the plasmid could be advantageous in situations wherein it is desirable to restrict its dissemination to bacterial strains closely related to pseudomonads.

Development of Cloning Vector pRO1729. Many bacterial strains are naturally resistant to the antibiotics ampicillin or carbenicillin and therefore this natural resistance limits the use of these bacterial strains in genetic cloning experiments. It therefore is desirable to incorporate additional antibiotic resistance determinants into pRO1727 to provide alternative strategies for antibiotic selection in these instances. This was done for the cloning vector plasmid pRO1727 by the addition of a cleaved fragment of DNA which encodes resistance to the antibiotic, chloramphenicol. The source of this genetic material was the plasmid pBR325 described in Table 1. To effect this change, plasmid pRO1727 was cleaved with the restriction endonuclease PstI and BamHI. The objective here was to remove the fragment of DNA occurring between base pair coordinates 5125 through 0 and onto 375. This region was replaced with a piece from plasmid pBR325 similarly cleaved. However, the piece from pBR325 contained within its structure, a gene which encodes chloramphenicol resistance. A further characteristic of this region is the occurrence of a cleavage site for EcoRI within the gene for chloramphenicol resistance. The plasmid has a molecular size of about 2.9 kilobase pairs. Thus, insertion of hetero-DNA at this EcoRI site inhibits expression of the chloramphenicol phenotype. Accordingly, this site can be used for cloning in the manner using the carbenicillin and tetracycline resistance genes.

Plasmids pRO1727 and pRO1729 were tested for their host range in *Pseudomonas putida* strain PPO131. Plasmid DNA preparations that had been purified by centrifugation in CsCl and ethidium bromide isopycnic gradients was transformed into this bacterial strain. Transformants from such experiments were purified and assayed for their plasmid DNA content and were found to contain plasmids identical to those produced in *Pseudomonas aeruginosa* both with respect to their molecular size and the antibiotic resistances they encoded.

Figure 3:
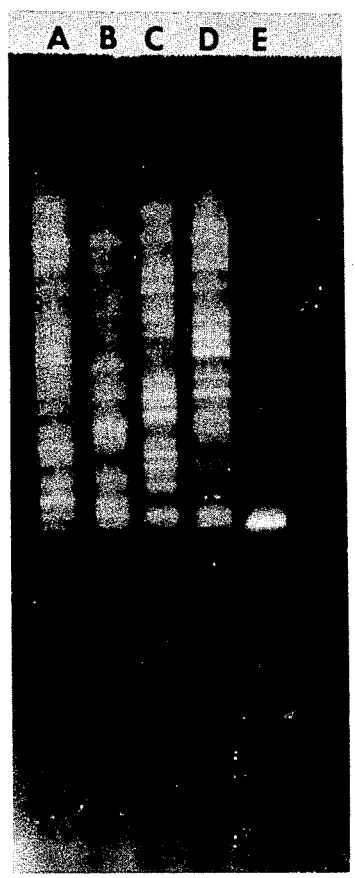
FIG. 3 is an agarose gel electrophoresis showing plasmid DNA obtained from cultures inoculated from mixed suspensions which contained independently isolated recombinant plasmids using the cloning vector pRO1727, using the method described previously in my application Ser. No. 328,957, filed Dec. 9, 1981 as discussed hereinafter.

Utility of pRO1727 for Cloning Using Direct Selection. The utility of pRO1727 for cloning of *Pseudomonas aeruginosa* PAO chromosomal DNA using the gene bank procedure described previously in Ser. No. 328,957. In this instance, however chromosomal and pRO1727 DNA was cleaved with restriction endonuclease PstI to test the performance of the vector, pRO1727, which now contained a single site for PstI cleavage in its genetic determinant for carbenicillin resistance. For this, DNA was cleaved, admixed, ligated and transformed into PAO2. When this was done and transformed bacterial colonies selected for growth on medium which contained 50 micrograms tetracycline per ml most of the colonies, 457 per 668 tested (69 percent), were found to be sensitive to the antibiotic, carbenicillin, indicating that PAO chromosomal DNA had been cloned into the PstI site located in the carbenicillin resistance determinant. Thus, the efficiency of cloning was high and approximately twice that previously reported for pRO1614 when cloning into its BamHI site. The 457 tetracycline sensitive transformed bacterial colonies where then pooled, grown in mixed culture and extracted for their plasmid DNA in the manner described in Ser. No. 328,957. These mixed-recombinant plasmid DNA preparations derived from four mixed cultures were electrophoresed and are displayed in FIG. 3. Files A, B, C, and D are from the recombinant plasmid DNA preparations. File E shows the vector pRO1727, without cloned DNA. Files A, B, C, and D clearly show the desired result. The presence of a multiplicity of plasmids of disparate size and genetic content.

The plasmids of the present invention have been deposited with the Northern Regional Research Laboratories of the United States Department of Agriculture in Peoria, Ill. and are freely available to the public upon request as follows:

pRO1727 as carried in *Pseudomonas aeruginosa* NRRL-B-15119.

pRO1729 as carried in *Pseudomonas aeruginosa* NRRL-B-15120.

I claim:

1. The plasmid pRO1727 ligated to other deoxyribonucleic acid segments.

2. The recombinant deoxyribonucleic acid plasmid pRO1729 alone or ligated to other deoxyribonucleic acid segments and derived from the plasmid pRO1727 of claim 1 with a first deoxyribonucleic acid segment between base pairs 5125 to 375 moving clockwise on the pRO1727 plasmid shown in FIG. 1 which has been deleted using PstI and BamHI and replaced with a second deoxyribonucleic acid segment ligated in place of the first segment produced by PstI and BamHI restriction endonuclease on pBR325, and specifying chloramphenicol antibiotic resistance in a site cleaved by EcoRI in the segment from pBR325.

3. The plasmid pRO1729 ligated to other deoxyribonucleic acid segments.

4. A plasmid pRO1727 isolated from *Pseudomonas aeruginosa* NRRL-B-15119.

5. A plasmid pRO1729 isolated from *Pseudomonas aeruginosa* NRRL-B-15120.

6. *Pseudomonas aeruginosa* NRRL-B-15119 containing plasmid pRO1727.

7. *Pseudomonas aeruginosa* NRRL-B-15120 containing plasmid pRO1729.

* * * * *